United States Patent
Zhang et al.

[11] Patent Number: 5,667,469
[45] Date of Patent: Sep. 16, 1997

[54] STRONG MAGNETISM THERAPEUTIC APPARATUS WITH PERMANENT-MAGNETS ROTATING AT LOW FREQUENCY

[76] Inventors: Xiaoyun Zhang, Suite 302, Duyue Bldg., Shenzhen University, Nanout District, Shenzhen, Guangdong 518060, China; Dali Zheng, Mid. Entr. 1 Suite 603, No. 22 Bldg. No. 76 Xueyuan nan Road, Beijing 100081, China; Weide Zhang, Suite 302, Duyue Bldg., Shenzhen University, Nantou District, Shenzhen, Guangdong 518060, China

[21] Appl. No.: 599,402

[22] Filed: Oct. 13, 1995

[30] Foreign Application Priority Data

Oct. 8, 1993 [CN] China ............... 93 1 18017.1

[51] Int. Cl.⁶ ............... A61B 17/52; A61N 2/00
[52] U.S. Cl. ............... 600/9
[58] Field of Search ............... 600/9–15

[56] References Cited

U.S. PATENT DOCUMENTS

| | | | |
|---|---|---|---|
| 4,537,181 | 8/1985 | Shalhoob et al. | 128/1.3 |
| 5,529,568 | 6/1996 | Rayman | 600/9 |

FOREIGN PATENT DOCUMENTS

| | | | |
|---|---|---|---|
| 86-206534 | 12/1987 | China . | |
| 88-216746 | 8/1989 | China . | |
| 2044499 | 9/1989 | China . | |
| 1062473 | 7/1992 | China . | |
| 3605899 | 8/1987 | Germany | 600/9 |
| 004230661 A1 | 3/1994 | Germany | 600/9 |

*Primary Examiner*—Jennifer Bahr
*Assistant Examiner*—Samuel Gilbert
*Attorney, Agent, or Firm*—Sughrue, Mion, Zinn, Macpeak & Seas

[57] ABSTRACT

This invention provides a strong magnetism therapeutic apparatus with permanent-magnet sets rotating at low frequency in which a base set made of magnetic material is fixed on a plate capable of rotating in both direction and at least two adjacent permanent-magnet sets for producing strong magnetic field are secured to said base set and separated by a isolating block made of non-magnetic material. A pole head is secured to the upper surface of each permanent-magnet set. The penetrating depth within the object to be treated is up to 500 mm. When used as a therapeutic instrument, this apparatus can produce desirable analgesic effect for late patient of, for example, cancer without the minus effect of radiation therapy and chemotherapy. The apparatus has also wide application in biologic and chemical field.

10 Claims, 5 Drawing Sheets

5,667,469

STRONG MAGNETISM THERAPEUTIC APPARATUS WITH PERMANENT-MAGNETS ROTATING AT LOW FREQUENCY

This is a continuation of International Application No. CN94/00077 filed Oct. 8, 1994.

FIELD OF THE INVENTION

This invention relates to a magnetic treating apparatus, and more particularly relates to a strong magnetism therapeutic apparatus with permanent-magnets rotating at a low frequency.

BACKGROUND OF THE INVENTION

It has been proved by modem research that magnetism has significant influence upon human body as well as other living things, water, and chemical materials. Existing magnetism therapeutic apparatus usually includes one or more pair of permanent-magnets for producing static magnetic field, and the object to be treated is placed at a position Surrounded by said permanent-magnets. Magnetic field produced in this manner (as shown in FIG. 1 and 2) can either penetrate uniformly into the object to be treated, or act only on the outer surface of the object. Since, on the one hand, the magnetic field is not variable and therefore has less effective on the object to be treated, on the other hand, it is impossible to concentrate magnetism specifically on predetermined position to be treated. The known apparatus are not able to produce significant treating results.

A magnetism therapeutic apparatus provided by Chinese Patent No. 88216746.4 includes three permanent-magnets with a conical front portion and a cylindrical rear portion. Said three permanent-magnets are fixed on a rotatable support which is driven by a motor to produce rotating magnetic field. The same poles of the three permanent-magnets are arranged in such a manner that their magnetic lines are concentrated to the forward tip of a main magnetic needle located at the central point of the three magnets, so as to form a magnetic beam. This kind of magnetism therapeutic apparatus can only be used to treat limited portion of human body, for example acupuncture points, and is not suitable for treating inside organs of human body because the volume of its permanent-magnets is not large enough.

Chinese patent No. 86206534 provides a magnetism therapeutic apparatus including a number of cylindrical permanent-magnets which are fixed on a rotatable means driven by a motor to produce rotating magnetic field. Said cylindrical permanent-magnets have a diameter of 8–12 mm and a height of 5–10 mm and are made of magnetic material with superior magnetic properties, therefore a relatively strong magnetic intensity may be obtained. However, since said cylindrical permanent-magnets are still small in volume, therefore this kind of apparatus is only suitable for treating some illness like pain caused by strike, dizzy, rheum-arthritis, etc.

U.S. Pat. No. 4,537,181 provides a magnetism therapeutic apparatus which includes a number of curved permanent-magnets fixed on a rotatable table driven by a motor to produce a rotating magnetic field. This kind of apparatus normally produces a magnetic field of 50 gauss at the portion to be treated, and is specifically designed for reducing pain caused by arthritis.

In conclusion, the analgesic effect of magnetism therapy is well known. The existing therapeutic apparatus, however, have only limited treating effect on pain occurring at some shadow portions of a patient and are not effective on pain from inside organs of human body, such as severe pain of a late patient of cancer, because those apparatus do not make use of large magnets and particularly there is no adequate technique available in the prior art to concentrate and unify the magnetic lines produced by magnets, which is indispensable for large magnet to be used in this kind of apparatus. As a general rule, the magnetic intensity will decrease rapidly once leaving away from the surface of a magnet, which in turn will limit treating depth and width of magnetism therapy. In addition, the treating depth and width of magnetism therapy may not be adjusted in known apparatus.

SUMMARY OF THE INVENTION

The main object of the present invention is to solve the aforementioned problem existing with the prior art by providing a magnetism therapeutic apparatus with permanent-magnets rotating at low speed. By means of the specially designed magnetic circuit of the present invention, the magnetic field constituted by said apparatus has intensive concentration and high uniformity, and either the treating depth or the treating width of this apparatus is superior to that of existing apparatus. Moreover, the effective treating depth is adjustable within the scope of 0–500 mm, while the treating width is adjustable from several cm to several hundreds of cm.

According to this invention, at least two sets of permanent-magnets separated by an isolating block made of non-magnetic material are secured to a base seat made of magnetic material which is rotatable in both direction. The upper surface of the two adjacent permanent-magnets are of opposite polarity. Said permanent-magnets consist of a large number, e.g. from several hundreds to several thousands, of small magnetic steel combined together. At least one conical pole head made of magnetic material is overlaid on the upper surface of said permanent-magnet sets to concentrate and unify magnetic line of force produced thereby. Generally speaking, magnetic intensity depends upon the volume of permanent-magnet, the larger the permanent-magnet is, the stronger the magnetic intensity will be. Since the relative large permanent-magnet sets used in this invention are combined by many small permanent-magnets, the magnetic intensity near its outer surface is not even. To solve this problem, a pole head is added to unify the magnetic intensity above the pole head. In this manner, a magnetic circuit consisting of said permanent-magnet sets, pole head and base seat will produce magnetic field perpendicular to the plane where the rotatable base seat resides. While the object to be treated remains statically within the magnetic field produced by this apparatus, magnetic lines penetrate the object in a varying manner with the rotation of the permanent-magnet sets to cause the electrons, conductive ions as well as other particles within the object to move virtically, and therefore produce desirable treating effect.

In order to solve the problem that magnetic intensity will reduce rapidly once the magnetic lines leaving away from the pole head, a high coercive force permanent magnet is placed between the opposing poles of two adjacent permanent-magnet sets to produce a magnetic field with its direction opposite to that of magnetic field produced by said permanent-magnet sets. By means of said high coercive permanent-magnet, the magnetic lines produced by said permanent-magnet sets will be forced to extend perpendicularly away from the pole head. As a result, the magnetic intensity in front of the pole head will not attenuate rapidly, so that the object to be treated will reside in a relatively strong magnetic field and the penetrating depth of magnetic lines into the object will be increased.

In order to keep the object to be treated, particularly a human body, stable in the magnetic field produced by this apparatus, a supporting plate is provided over said pole head. Said supporting plate has four extendible legs standing on ground. Said supporting plate and its legs constitute a platform. Said legs are surrounded by a protective plate of the thick of 5-12 mm to form a kind of frame. The supporting plate and protective pate may be made of aluminum, plastic, resin, veneer board, felt, etc. or a combination of two or more of these materials. The platform has to be stable, solid and safe structure, and has the functions of shock absorbing, noise elimination, heat dissemination, and preventing the magnetic field from dissemination.

In order to make the platform more flexible, it may consist of a main table and a movable table. The movable table is made of light material such as wood and may be moved rationally.

In order to increase the extending range of magnetic lines, a magnetic inductive plate is suspended at a position directly above the platform. Magnetic lines generated upward from one of the two permanent-magnet sets will be conducted by the magnetic-inductive plate, and then go downward to another permanent-magnet set so as to ensure that as many as possible magnetic lines can pass through the space above the platform, and the magnetic field acting on the object at the platform has sufficient magnetic intensity.

The effective magnetic field passing through the object on said platform, i.e. the effective treating depth and treating width, depend to certain degree on the volume, terminal area and shape of the permanent-magnet sets and the area of the pole head. The larger the volume is, the deeper the treating depth will be; the larger the terminal area is, the larger the treating width will be. The permanent-magnet sets may have rectangular or trapezoidal section. When pole heads with trapezoidal section are used, the pole head should be attached to the end of the permanent-magnet with smaller terminal surface. Under the condition of same volume and same sectional area, the permanent-magnet sets with trapezoidal section will produce stronger magnetic intensity than that of rectangular one. The oblique angle of the side surface of the trapezoidal permanent-magnet sets can be selected within the range of 45-90 degree according to experience, and preferably be 60 degree.

The pole heads may also have trapezoidal section with their bottom surface of larger area secured to the permanent-magnet sets. The pole heads function to unify and concentrate magnetic lines produced by the permanent-magnet sets, and therefore has important influence over the treating depth and width of this apparatus. The oblique angle of the side surface of the pole head can be selected within the range of 30-45 degree, and preferably be 45 degree. The larger the terminal area of the pole head is, the wider the treating width will be. The pole head with trapezoidal section may have a structure of multiple layers combined together. When it is necessary to increase the effective treating area of this apparatus, one or more top layers of the combined pole head may be removed so as to increase the exposed area of the pole head. On the other hand, when deeper treating depth rather than large treating width is needed, one or more top layers may be added to the combined pole head. In the latter case, the magnetic lines can be concentrated more strongly by means of the pole head with smaller terminal area.

According to the principle that magnetic intensity will increase when decreasing the distance apart from permanent-magnet sets, the treating depth may also be adjusted by changing the distance between said platform and pole heads. This can be achieved by changing the length of the extendible legs.

The rotating speed of the low frequency magnetic field, so as the permanent-magnet sets according to this invention is about 0-45 rpm, preferably 20 rpm.

The permanent-magnet sets used in this invention is made of rare earth materials with high permeability.

When objects other than human body are treated, the platform may be replaced by automatic or semi-automatic transporting mechanism of crawled-type.

DESCRIPTION OF THE DRAWINGS

The present invention will be described in further detail with reference to the accompanying drawings, wherein.

DETAILED DESCRIPTION OF THE INVENTION

Figure 1:
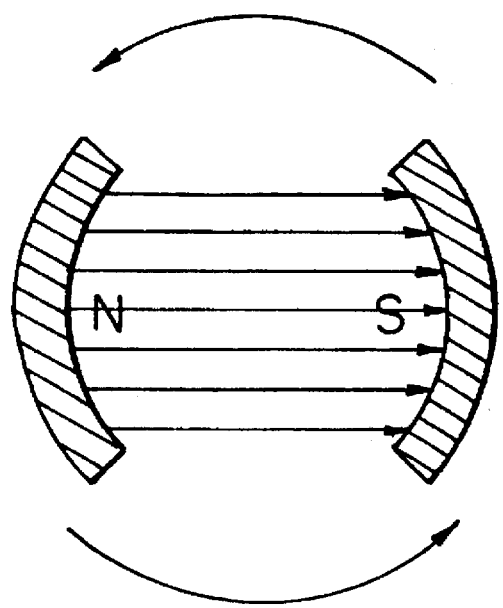
FIG. 1 is a schematic view showing the static magnetic field produced by a pair of permanent-magnet.
Figure 2:
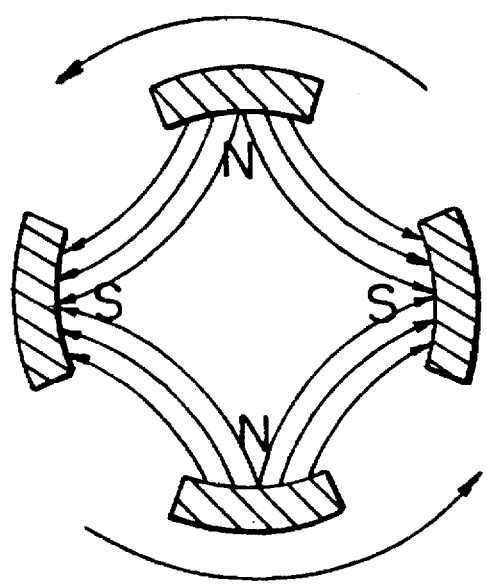
FIG. 2 is a schematic view showing the static magnetic field produced by two pairs of permanent-magnet.
Figure 3:
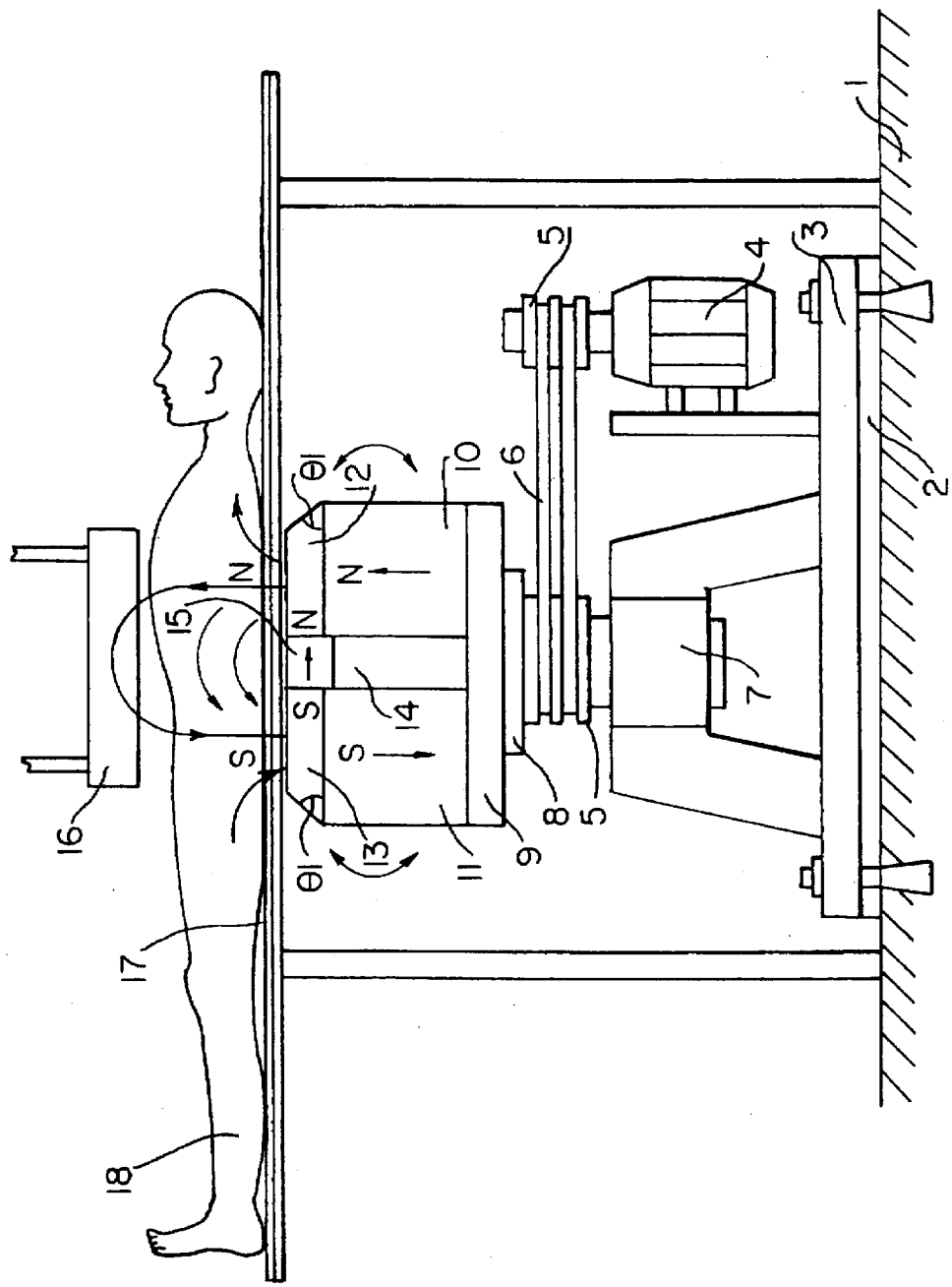
FIG. 3 is schematic view showing the structure of a magnetic therapeutic apparatus according to one embodiment of the present invention.

Embodiment 1:

As shown in FIG. 3, a layer of hard rubber 2 for absorbing shock and a base plate 3 are fixed by upset bolts on solid ground area 1. A speed-adjustable motor 4 is mounted on the base plate 2 to drive the permanent-magnet sets through a belt pulley 5 and belt 6 to rotate at a speed of 20 rpm in a horizontal plane. A rotating shaft 7 passes through a bearing hole of a bearing-supporting frame with its axis extending in vertical direction. A horizontal plate 8 made of magnetic material is fixed to the top end of the rotating shaft 7, and a rectangular base seat 9 made of magnetic material is mounted on the upper surface of the horizontal plate 8. A pair of rectangular permanent-magnet sets 10 and 11 are fixed respectively by means of adhesive to the opposing sides of the upper surface of the rectangular base seat 9. The magnetic pole N of the permanent-magnet set 10 and the magnetic pole S of the permanent-magnet set 11 are located upward. Pole heads 12 and 13 made of magnetic material are overlaid on the upper surface of the permanent-magnet 10 and 11. Said pole head 12 and 13 have trapezoidal section, and the oblique angle O1 of the side wall of the pole head 12 and 13 with respect to their bottom surface is about 45 degree. A gap is formed between the permanent-magnet sets 10 and 11, and an isolating block 14 made of non-magnetic material is inserted into the gap. The isolating block 14 has a width corresponding that of the gap, and the upper surface of the isolating block 14 should not be higher than the upper surface of the permanent-magnet sets 10 and 11 after being inserted therein between. A permanent-magnet 15 with a width corresponding to that of the gap is overlaid on the isolating block 14 and is made of a material with high permeability. The upper surface of the permanent-magnet 15 is coincident with that of pole head 12 and 13. The magnetic pole N of the permanent-magnet 15 is oriented toward the permanent-magnet set 10 so as to produce a magnetic field opposing to that produced by permanent-magnet sets 10 and 11. A magnetic-inductive plate 16 made of magnetic material is suspended directly above the pole heads 12 and 13 by a supporting frame in the form of a suspension arm. A horizontal platform 17 is located between said plate 16 and pole heads 12 and 13. Said platform 17 stands on ground by extendible legs connected to each corner of the platform. The object to be treated, such as a patient 19 as shown in FIG. 3, is laid down on the platform 17 with the treated portion positioned between two pole heads 12, 13 and plate 16. When the power supply is on, the motor 4 rotates and the treatment started.

Figure 4:
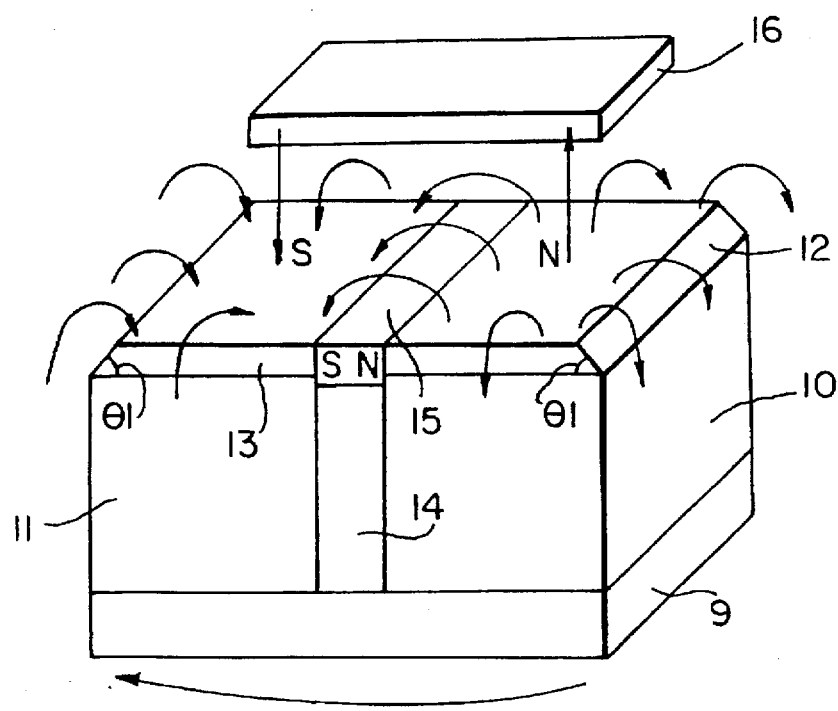
FIG. 4 is a schematic view showing the magnetic field produced by a pair of rectangular permanent-magnet sets according to the present invention.

As shown in FIG. 4, the magnetic circuit of this apparatus consists of permanent-magnetsets 10 and 11, pole heads 12 and 13, magnetic-inductive plate 16, and base seat 9. Magnetic lines generated from the permanent-magnet set 10 will at first radiate toward plate 16 in a down-to-up direction and penetrate the pole head 12 and the object 18 to be treated, then they will be conducted by the plate 16 and go down to permanent-magnet set 11 through said object 18 and magnetic head 13, and finally return to permanent-magnet set 10 through the base seat 9 to form a closed magnetic path. The horizontal plate 8 is driven by the motor 4 and rotates at a speed of 20 rpm.

Since the direction of magnetic field produced by the permanent-magnet 15 is opposite to that of said magnetic path, magnetic lines from the pole head 12 are forced to pass upward to penetrate the object 18, rather than return directly back to pole head 13. As a result, the magnetic field at the location of said object 18 is enhanced.

Figure 7:
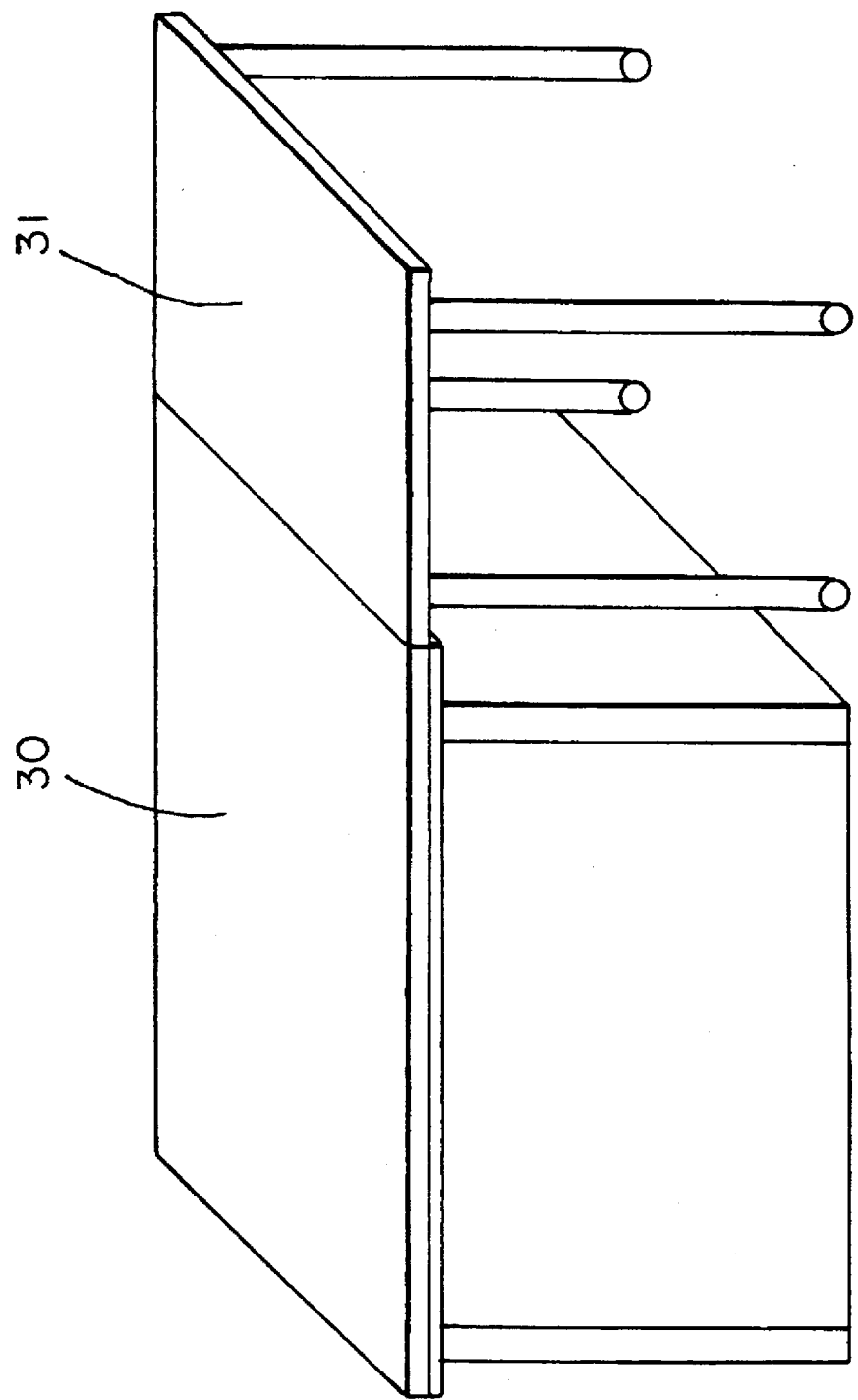
FIG. 7 is a schematic view showing the platform consisting of a main table and a movable table.

Said platform 17 may also be a table consisting of a main table 30 and a movable table 31 as shown in FIG. 7.

Figure 5:
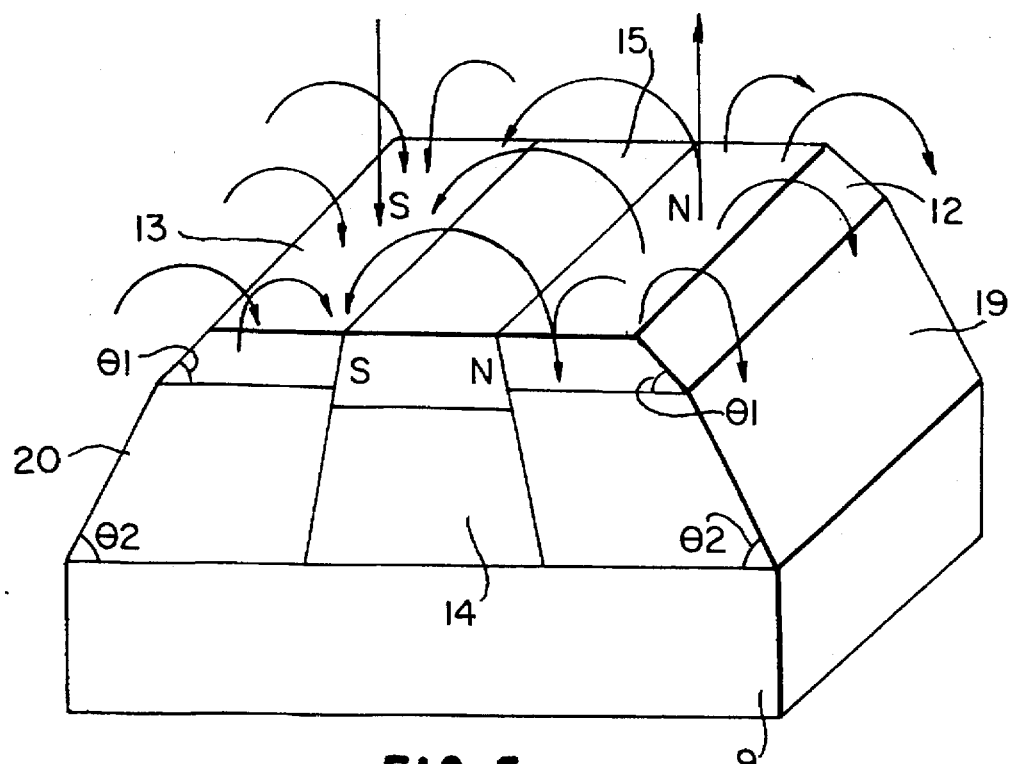
FIG. 5 is a schematic view showing the magnetic field produced by a pair of permanent-magnet sets with a trapezoidal section according to the present invention.

Embodiment 2:

As shown in FIG. 5, the apparatus of this embodiment 2 is similar to that of the first embodiment except the rectangular permanent-magnet sets 10, 11 are replaced by trapezoidal permanent-magnet sets 19, 20, and the oblique angle θ2 is 60 degree.

Figure 6:
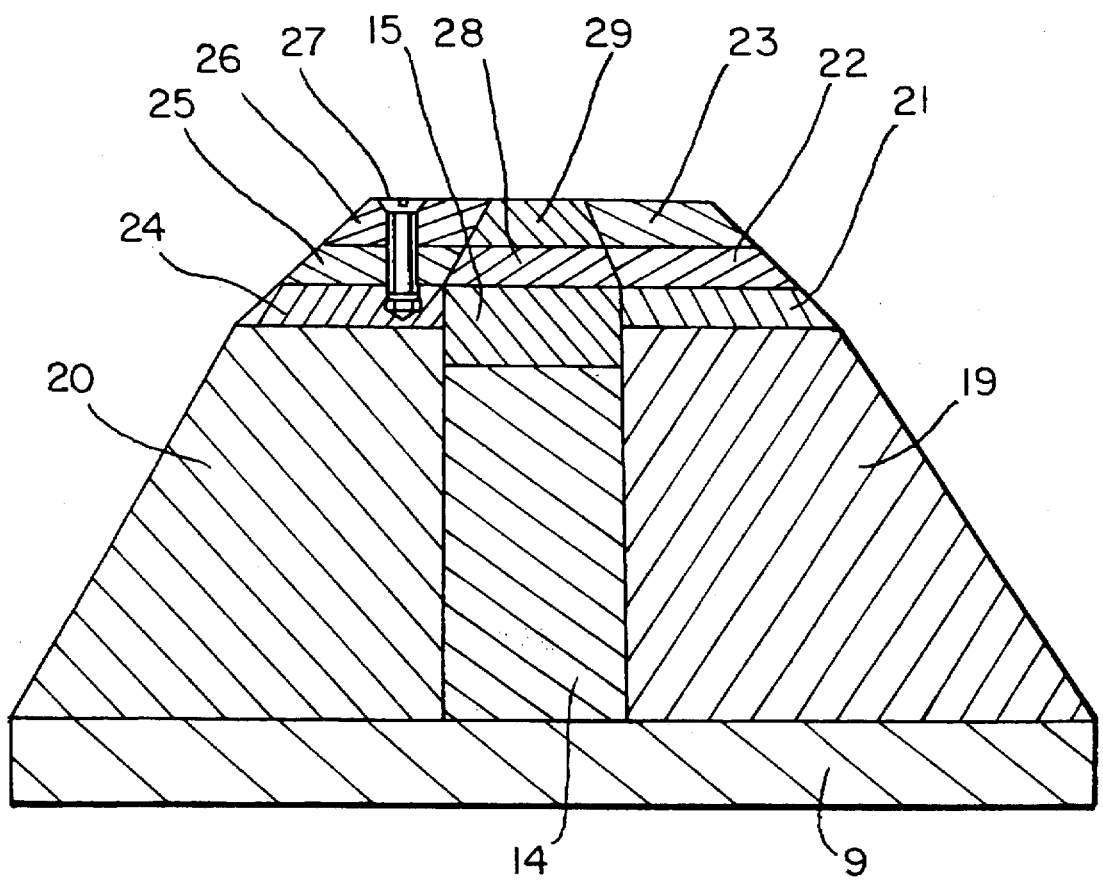
FIG. 6 is a sectional view showing the three layered structure of the pole head of the permanent-magnet as shown in FIG. 5.

Embodiment 3:

As shown in FIG. 6, on the basis of embodiment 2, the pole head 12 is replaced by a three-layered pole head 21, 22, 23, and pole head 13 replaced by a three-layered pole head 24, 25, 26, wherein pole head 21 and 24 are adhered respectively to the upper surface of the permanent-magnet sets 19 and 20. The pole head 22, 23 and 24, 25 are mounted respectively on the upper surface of the pole head 21 and 24 by means of 4 screws 27. The opposing inner sides of the pole head 22, 23, 24 and 24, 25, 26 have a oblique angle of 3 for forming a dovetail groove. A permanent-magnet 15 with high permeability is adhered on the isolating block 14 inserted into the gap between the permanent-magnet sets 19 and 20. The upper surface of the permanent-magnet 15 is coincident with the upper surface of the pole head 21 and 24. Two permanent-magnets 28, 29 with high coercive force are overlaid on the permanent-magnet 15 and have a section suitable for fitting with the aforementioned dovetail groove. When relative large treating area is needed, the pole head 23, 26 and coercive force permanent-magnet 29 may by removed by releasing the screw 27. The treating area may be increased further by taking away the pole head 22, 25 and high coercive force permanent-magnet 28 in similar manner.

INDUSTRIAL APPLICATION

Due to the fact that the magnetism therapeutic treating apparatus according to this invention makes use of permanent-magnet sets made of rare earth material with high permeability, and the upper surface of said permanent-magnets is provided with a pole head, and both the permanent-magnets and pole head have a specially designed shape and structure, therefore the apparatus can provide a magnetic field with its magnetic intensity up to 0.1–0.8 T, an effective penetrating depth up to 500 mm, and an effective treating diameter up to 950 mm. This apparatus can produce desirable analgesic effect for late patient of, for example, cancer without the minus effect of radiation therapy and chemotherapy. Since the permanent-magnet sets used in this apparatus rotate at a low speed, the magnetic field produced thereby exerts neither negative influence upon normal cell tissue nor discomfortable felling upon human body. In addition to analgesic effect, the magnetic field produced by the apparatus of this invention has the following therapeutic effect:

(1) speeding up recovery of a wound;

(2) promoting metabolism of normal cell;

(3) adjusting normal metabolism of malformation organism and regeneration of leukocyte, delaying development of cancer;

(4) promoting soften metabolism oft he obstructive tissue of cardiovascule;

(5) promoting normal growth of hemoglobin, increasing the efficiency of oxygen supply;

(6) promoting normal activity of conductive ions within the human body;

(7) assisting pacemaking of patient of heart-disease;

(8) promoting relax of memory nerve;

(9) promoting normal growth of embryo.

The apparatus according to this invention has the following biological applications:

(1) growth of cell;

(2) incubation of egg;

(3) organism experiment for seed of plant or egg cell of animal;

The apparatus according to this invention has the following application in chemistry:

(1) activation of water;

(2) speeding up the alcoholization of wine;

(3) speeding up chemical reaction;

(4) treatment of medicine.

While the present invention has been particularly described with reference to a preferred embodiments, it would be understood by those skilled in the art that various changes in form and detail may be made without departing the spirit and scope of the present invention as defined by the accompanying claims.

We claim:

1. A magnetic therapeutic apparatus with a set of permanent-magnets rotating at low frequency, comprising: a base seat made of magnetic material fixed on a plate capable of rotating in both clockwise and counterclockwise directions, at least two permanent-magnets for producing a strong magnetic field secured to said base seat and separated by an isolating block made of non-magnetic material, upper surfaces of said two permanent-magnets being of opposite magnetic polarity, at least one pole head made of magnetic material secured respectively to the upper surface of each permanent-magnet, a permanent-magnet with high coercive force fixed between opposite magnetic poles of said two permanent-magnets, wherein the direction of the magnetic field produced by said high coercive force permanent-magnet is opposite to that of the magnetic field produced in a magnetic path constituted by said base seat, the two permanent-magnets, and the pole heads, and driving means connected to the plate for rotating said plate.

2. A magnetic therapeutic apparatus according to claim 1, wherein the rotating speed of said rotatable plate driven by said driving means is 0–45 rpm.

3. A magnetic therapeutic apparatus according to claim 1, wherein a supporting plate is provided over said pole head and has four extendible legs standing on ground, said supporting plate and said legs constituting a platform, said legs being surrounded by a protective plate made by one of the following materials: aluminum, plastic, resin, veneer board, or felt, or a combination of two or more of those materials to form a protective frame.

4. A magnetic therapeutic apparatus according to claim 3, wherein a magnetic-inductive plate is provided at a position directly above said platform.

5. A magnetic therapeutic apparatus according to claim 4, wherein said magnetic-inductive plate is carded by a suspension arm.

6. A magnetic therapeutic apparatus according to claim 1, wherein said pole head has trapezoidal section, a relatively large bottom surface of said pole head having a shape and dimensions corresponding to those of said upper surface of said permanent-magnets, and an oblique angle of a side surface of said pole head is 45 degrees.

7. A magnetic therapeutic apparatus according to claim 6, wherein said pole head has a multi-layered structure, the connection between the multiple layers being achieved by screws and the attracting force of the permanent-magnets.

8. A magnetic therapeutic apparatus according to claim 1, wherein said two permanent-magnet sets secured to said base seat are rectangular permanent-magnet sets.

9. A magnetic therapeutic apparatus according to claim 1, wherein said two permanent-magnets secured to said base seat are trapezoidal.

10. A magnetic therapeutic apparatus according to claim 9, wherein an oblique angle of a side surface of the trapezoidal permanent-magnets is 60 degrees.

* * * * *